United States Patent [19]
Shanbrom

[11] Patent Number: 6,093,401
[45] Date of Patent: Jul. 25, 2000

[54] NATURAL COLOR CONCENTRATES AND ANTIMICROBIAL NUTRACEUTIAL FROM PLANTS

[75] Inventor: Edward Shanbrom, Santa Ana, Calif.

[73] Assignee: Shanbrom Technologies LLC, Ojai, Calif.

[21] Appl. No.: 08/931,315

[22] Filed: Sep. 16, 1997

[51] Int. Cl.$^7$ .............. A01N 65/00; A23C 9/14; A23B 4/03; A23L 3/34
[52] U.S. Cl. ............ 424/195.1; 426/271; 426/531; 426/443
[58] Field of Search .............. 424/195.1; 514/449, 514/451, 783; 426/271, 272, 531, 537, 549, 550, 599, 615, 419, 443, 489

[56] References Cited

U.S. PATENT DOCUMENTS

| | | | |
|---|---|---|---|
| 4,405,323 | 9/1983 | Auerbach | 604/285 |
| 5,474,774 | 12/1995 | Walker et al. | 424/195.1 |
| 5,683,678 | 11/1997 | Heckert et al. | 424/52 |

FOREIGN PATENT DOCUMENTS

| | | |
|---|---|---|
| 5017372 | 1/1993 | Japan . |
| 8205023 | 4/1983 | South Africa . |

OTHER PUBLICATIONS

Van Teeling et al. "Chromatography of anthocyanins on columns f insoluble poly(vinylpyrrolidinone)," J. Chromatographic Sci. (1971) 9(8): 505–9 (abstract only), 1971.

Nawa et al. "Production of Anthocyanins, Carotenoids, and Proanthocyanindins by cultured cells of Rabbiteye Blueberry (Vaccinium ashei Reade", Biosci. Biotech. Biochem. (1993) 57(5): 770–4, 1993.

*Primary Examiner*—Jean C. Witz
*Assistant Examiner*—Susan Hanley
*Attorney, Agent, or Firm*—Graham & James LLP

[57] ABSTRACT

An active coloring concentrate can be prepared from the juice of cranberries and blueberries by treating juice or homogenate with an appropriate binding matrix. Assorted ion exchange resins such as cholestyramine are effective binding matrices, but the currently preferred material is a food grade of cross-linked polyvinyl pyrollidone. The binding matrices are used to concentrate active materials from cranberry and a colored solid is produced. This substance shows anti-bacterial and anti-viral properties. It can be readily consumed as a therapeutic or nutraceutical, used as a coloring agent, or it can be used topically. Significant amounts of active concentrate can be produced from cranberry presscake which is normally a waste material.

12 Claims, No Drawings

NATURAL COLOR CONCENTRATES AND ANTIMICROBIAL NUTRACEUTIAL FROM PLANTS

BACKGROUND OF THE INVENTION

1. Field of the Invention

The current invention concerns the field of natural products and foods and more specifically colors and an antimicrobial composition prepared from cranberry juice.

2. Description of Related Art

Health foods are estimated to currently represent an annual market in the United States of at least ten billion dollars ($10,000,000,000.00). By health foods is meant vitamins, minerals and herbal products that are widely believed to be efficacious in improving human health without the cost and side-effects of ordinary pharmaceuticals. In recognition of the popularity and importance of these products the term "nutraceutical" has been coined and the product category has received special government regulatory treatment.

There can be no denying that vitamins and minerals are essential for normal human health. Whether "excessive" doses of some vitamins, for example Vitamin C, provide special benefits is more controversial. More controversial still are the many herbal products of recent popularity such as saw palmetto and *Ginkgo biloba*. Many people swear by these and related products while large pharmaceutical companies claim that these remedies are untested and worthless. Nevertheless, virtually all important pharmaceutical drugs are based on natural plant products. Not too long ago the study of botany was a mandatory part of medical education. It is also clear that at least some of the herbal cures are effective. For example, feverfew, long a folk cure for headaches, is currently used in Europe as a legitimate cure for migraines.

An even more widely known "natural cure" is the use of fruit juices, especially cranberry juice, for treatment and prevention of urinary tract infections. While the "cranberry juice cure" is widely prescribed, the precise basis of its effectiveness is not completely known. An early hypothesis was that the natural fruit acids, such as benzoic acid, acidified the urine and thereby inhibited bacterial proliferation. While acidification may be part of the puzzle, it does not seem sufficient to explain the advantage cranberry juice seems to hold over other acidic fruit juices. More recently there have been a number of reports that fruits of cranberry and related species of the genus Vaccinium contain a potent factor that inhibits bacterial adhesion. Since bacterial must be able to adhere to urinary endothelia to cause an infection, the anti-adhesion factor may explain the cranberry effect.

In fact, at least one research group has put extensive efforts into purification of the anti-adhesion factor from cranberry and related fruits. The reader's attention is drawn to a series of U.S. patents to Walker et al. (E. B. Walker, R. A. Mikelsen, J. N. Mikelsen and B. L. Roth) (including U.S. Pat. Nos. 5,474,774, 5,525,341, and 5,646,178). These patents disclose complex extraction and fractionation processes by which cranberry fruits are extracted and yield a fraction enriched in the before-mentioned anti-adhesion factor. These patents provides tentative identification of the anti-adhesive factor.

However, the Walker et al. process is complex and cumbersome. Further, it is not clear that all the benefits of cranberry and related fruits is due to the anti-adhesion factor. Therefore, there is still a need for a simple method to concentrate effective materials from cranberry and other plant materials (e.g., flowers, fruits, leaves, stems and roots) for nutraceutical and other uses. Besides their curative properties fruits and other plant materials are frequently strongly pigmented. Since much of our food is of plant origin people have become used to having foods with bright and appealing colors. Highly processed "artificial" foods are generally colorless or have drab and unappealing colors.

Therefore, many millions of dollars each year are spent on putting "artificial colors" and "artificial flavors" into processed food products. While such additives may make the processed food products more attractive, they actually make the products even less suitable for human consumption. The worst of the carcinogenic coal tar dyes have been removed from the market, but a lingering doubt surrounds many of the remaining "certified food colors." Thus, there is a significant need for methods to capture natural colors and flavors from fruits and vegetables.

SUMMARY OF THE INVENTION

An active concentrate can be prepared from the juice of cranberry and other fruits or vegetables by treating the juice with an appropriate binding matrix. Assorted ion exchange resins such as cholestyramine are effective binding matrices, but the currently preferred material is a food grade of polyvinyl pyrollidone cross-linked, especially in a cross-linked form. When appropriate binding matrices are used to concentrate active materials from cranberry, a colored solid is produced. This substance shows significant anti-bacterial and anti-viral properties. It can be readily consumed as a nutraceutical, it can be used topically, or it can be used as a safe food coloring. An additional advantage of the present method is that significant amounts of active concentrate can be produced from cranberry presscake which is normally a waste material. This same method is adapted to concentrating colors and flavors from a variety of fruits and vegetables.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a method for concentrating colors and flavors from fruits and vegetables (including flowers, leaves, stems, roots and "teas") and an anti-microbial extract from cranberry and other fruit juices.

The present inventor has a long record of inventions in the medical field particularly in processes to disinfect blood and blood products. It was only natural that he would turn his inventive energies to the food industry where similar problems of dangerous pathogens exist. One has only to read recent headlines concerning deaths and illnesses caused by bacterially contaminated fruit juice to see the logical application of improved disinfection to foods. Part of the methods used by the present inventor involve adding effective amounts of disinfectant such as iodine and then removing them after an adequate disinfection period so that the final product while disinfected contains no disinfectant. Various organic polymers such as ion exchange resins and insoluble polyvinyl pyrollidone (PVP) have proved to be effective iodine removal agents.

In the course of perfecting disinfecting purification methods for fruit juices the present inventor noticed that the iodine removal agents often removed some of the fruit juice color along with the iodine. This resulted in the question of whether these removal methods might be useful for concentrating fruit color or flavor or some other juice component. A considerable number of different juices and binding agents were, therefore, experimented with. These concentrated materials are useful as color or flavor additives for food products. In addition, it has been discovered that some of the concentrates have unexpected properties.

EXPERIMENT 1

Table 1 shows whether cranberry juice color is appreciably bound by a number of different binding materials. For this experiment 1 g samples of each of the listed materials were mixed into 25 ml aliquots of ordinary cranberry juice. The materials were mixed for 30 min after which the juice was decanted and the material washed with water and inspected for binding of color. Of course, it is possible that some of the matrices bound uncolored cranberry components.

TABLE 1

| Binding Matrix | Result |
| --- | --- |
| Sephadex G-25 | no binding |
| Polydex Resin | no binding |
| Cholestyramine | good binding |
| Purolite A-600 Resin | no binding |
| Purolite A-606 Resin | no binding |
| Purolite C-100 Resin | no binding |
| Purolite P-100 | no binding |
| Dextran (100,000 MW) | no binding |
| Dextran (75,000 MW) | no binding |

Insoluble (cross-linked) PVP is a well-known iodine binding agent; in addition, it is known to bind polyphenols and is used for this purpose in the food industry. Many plant derived pigments are polyphenols and might be expected to bind to insoluble PVP, but as far as the present inventor knows no one has taken advantage of this property to purify colors and flavors from plant materials. Table 2 shows the degree of binding (color) of a number of different juices to insoluble, crosslinked PVP and cholestyramine. All of the juices bound well to both of the binding matrices. Although observation of the juice following the experiment suggested that the PVP bound more color (i.e., the juice was significantly lighter than the corresponding cholestyramine-treated juice), the cholestyramine appeared significantly darker than the corresponding PVP as if it held more pigment. Twenty five milliliters of juice was reacted with 1 g of binding substance following the same procedure as used for the experiment of Table 1, above. In addition to the materials tested in Table 1, the inventor has also found that starch, cross-linked starch and carboxymethyl cellulose are effective at binding pigment factors from vegetable material.

TABLE 2

| Juice | XL-PVP | Cholestyramine |
| --- | --- | --- |
| Red Raspberry | +++ | +++ |
| Blackberry | ++ | ++ |
| Blueberry | ++ | ++ |
| Strawberry | ++ | ++ |
| Cherry | ++ | ++ |
| Cranberry | ++ | ++ |

EXPERIMENT 2

These "captured" fruit juice components were then tested to see if any of them exhibited significant antibacterial activity. For this experiment 100 ml suspensions of *Escherichia coli* and *Staphylococcus epidermidis* were made in phosphate buffered saline (PBS). One half gram samples of each of the bound fruit juice samples were weighed into sterile 15 ml tubes to which was added 10 ml of one of the bacteria suspensions. The tubes were mixed for 30 min at room temperature. An aliquot of each treated suspension was streaked onto a nutrient agar plate and incubated for 24 hours at room temperature. Table 3 shows the resulting bacterial growth. In this experiment most of the juice components showed either no or slight activity. Blueberry and cranberry, however, showed dramatic inhibition of both species of bacteria. This was somewhat unexpected because while the prior art teaches that these juices inhibit bacterial adhesion, it does not indicate that these material dramatically inhibit bacterial growth. It cannot be determined from this experiment whether the bacteria were simply killed by the incubation with the juice component or whether the juice component simply resulted in long term bacterial inhibition. A "rescue" experiment in which attempts are made to wash off the juice extract is needed to answer this question.

TABLE 3

| | E. coli | | S. epidermidis | |
| --- | --- | --- | --- | --- |
| Juice | PVP | Chol. | PVP | Chol. |
| Control | ++++ | ++++ | +++ | +++ |
| Red Raspberry | +++ | +++ | +++ | +++ |
| Blackberry | +++ | +++ | ++ | ++ |
| Blueberry | 0 | 0 | 0 | 0 |
| Strawberry | ++++ | ++++ | +++ | +++ |
| Cherry | ++++ | ++++ | +++ | +++ |
| Cranberry | 0 | 0 | 0 | 0 |

The results that showed strong antibacterial products for cranberry and blueberry juices were somewhat unexpected. It should be noted that blackberry shows a weaker antibacterial response against *S. epidermidis*. It is possible that blackberry and the other juices actually share the properties of cranberry albeit at a significantly lower concentration.

EXPERIMENT 3

The striking antibacterial results prompted the inventor to see whether the juice factors also had any antiviral properties. Only the cranberry and blueberry extracts were tested since they showed the most dramatic antibacterial effect. They were tested against equine myocarditis virus (EMC) which is an example of a moderately difficult to inactivate enveloped virus. Viral suspensions were prepared in both PBS and tissue culture medium to control for media effects. The test samples were prepared by suspending 0.5 g samples of the bound juice factors in 15 ml of virus suspension in PBS. The samples were incubated for 1 hour at room temperature (RT) and then serially diluted (titered) in a Virus End Point (VEP) assay cell line virus assay. That is, the diluted samples were added to animal cells in tissue culture plates. The cells were grown for 24 hours at 37° C. in 96 well culture plates in 5% $CO_2$ and were then read to determine presence of virus. The results shown in Table 4 indicate that both juices have moderate antiviral properties and are able to reduce the viral titer by at least one log. The other juice factors may also have antiviral properties although the appear to lack antibacterial properties as strong as cranberry and blueberry. It seems likely that a more efficient (e.g., chromatographic) method might capture a larger amount of the antiviral factor.

TABLE 4

| Dilution → | 1 | 2 | 3 | 4 | 5 | 6 | 7 | 8 | 9 | 10 | 11 | 12 | Titer |
|---|---|---|---|---|---|---|---|---|---|---|---|---|---|
| PBS Control | 4 | 4 | 4 | 4 | 4 | 4 | 2 | 0 | 0 | 0 | 0 | 0 | 4.9 |
| Medium Control | 4 | 4 | 4 | 4 | 4 | 4 | 4 | 0 | 0 | 0 | 0 | 0 | 5.2 |
| Cranberry Choles. | 4 | 4 | 4 | 4 | 1 | 0 | 0 | 0 | 0 | 0 | 0 | 0 | 3.3 |
| Cranberry PVP | 4 | 4 | 4 | 4 | 3 | 0 | 0 | 0 | 0 | 0 | 0 | 0 | 3.7 |
| Blueberry Choles. | 4 | 4 | 4 | 4 | 0 | 0 | 0 | 0 | 0 | 0 | 0 | 0 | 3.1 |
| Blueberry PVP | 4 | 4 | 4 | 4 | 2 | 0 | 0 | 0 | 0 | 0 | 0 | 0 | 3.5 |

The contact effectiveness of the fruit juice factors were explored by placing the bound fruit juice material into small (60 cc) columns and flowing various microbe containing solutions through. Two gram aliquots of cranberry PVP or cholestyramine or blueberry PVP or cholestyramine prepared as above were placed into each column. Suspensions were prepared in PBS of *E. coli, S. epidermidis* and EMC virus. Fifty milliliters of these suspensions were allowed to rapidly flow through each of the columns. The results of the earlier bacteria experiments were replicated in that there was no growth of either bacteria after passage through columns containing either blueberry or "cranberry factors." The control columns of PVP or cholestyramine alone showed no inhibition of the bacteria.

The results of the viral inactivation are shown in Table 5. The experiment was performed as before on a VEP assay. The only difference was that the column approach resulted in a somewhat higher viral inactivation than in the previous experiment. This indicates that rapid contact with the insolubilized juice factors is sufficient to result in significant viral inactivation.

TABLE 5

| Dilution → | 1 | 2 | 3 | 4 | 5 | 6 | 7 | 8 | 9 | 10 | 11 | 12 | Titer |
|---|---|---|---|---|---|---|---|---|---|---|---|---|---|
| Control | 4 | 4 | 4 | 4 | 4 | 4 | 4 | 2 | 0 | 0 | 0 | 0 | 5.6 |
| Cranberry Choles. | 4 | 4 | 4 | 1 | 0 | 0 | 0 | 0 | 0 | 0 | 0 | 0 | 2.6 |
| Cranberry PVP | 4 | 4 | 4 | 3 | 0 | 0 | 0 | 0 | 0 | 0 | 0 | 0 | 3.0 |
| Blueberry Choles. | 4 | 4 | 4 | 4 | 0 | 0 | 0 | 0 | 0 | 0 | 0 | 0 | 3.1 |
| Blueberry PVP | 4 | 4 | 4 | 4 | 0 | 0 | 0 | 0 | 0 | 0 | 0 | 0 | 3.1 |

EXPERIMENT 4

An additional way of assessing bacterial growth is by tubidometry. The light absorption or "optical density" of a solution is measured as an indication of bacterial growth. As the number of bacteria increases the amount of light absorbed or scatters also increases. In this experiment heavy suspensions of the same bacteria used in Experiment 2 were prepared in bacterial growth medium. Equal amounts of Cranberry-PVP or PVP (control) was added to each tube. The tubes were then incubated at room temperature for 24 hr. The original intent of the experiment was to measure the optical absorbance of the tubes as an assay of bacterial growth. However, all of the Cranberry tubes showed complete clearing indicating that all of the bacteria had been killed. The control tubes remained turbid indicating no bacterial kill.

There is some indication in the literature that a primary effect of cranberry juice is due to its acidity which can be inhibitory to bacteria. Tests made during production of the Cranberry-PVP indicate that a majority of the organic acids present in the fruit remain in the supernatant and are not captured by the PVP. Nevertheless, the Cranberry-PVP does have an acidic pH; therefore, 0.5 g samples of the material were neutralized with 0.5M sodium bicarbonate. The neutralization treatment caused the extract to turn very dark, almost black, from an original bright red color. Significantly, the neutralized material was just as effective at clearing the solutions indicating that pH is not a factor in the bactericidal properties of the extract.

EXPERIMENT 5

A classic test of antimicrobial materials is the "zone of inhibition" which develops around such materials when placed on a bacteria growth plate. In this experiment agar plates were swabbed with suspensions of *E. coli, Pseudomonas aeruginosa, S. aureus,* or *Bacillus subtilis*. Aliquots of Cranberry-PVP (1.0 g, 0.5 g, 0.25 g, or 0.1 g) were placed on the plates which were then incubated for 24 hr. In all cases at least an 8 cm inhibition zone (measured from the edge of the Cranberry-PVP extract) developed; the control PVP showed no inhibition. This indicates significant inhibitory properties. Neutralizing the material with 0.5 m sodium bicarbonate did not destroy the inhibitory properties.

EXPERIMENT 6

Finally, viral tests were repeated using varying amount of Cranberry-PVP. The extract was mixed with 10 ml of Vesicular Stomatitis Virus (VSV), different amounts of extract to each tube. After a 60 min incubation the material were tested on a VEP assay as above. The results were: 1.0 g extract gave a 5 log viral kill; 0.5 g gave a 5 log viral kill; 0.25 g gave a 3 log viral kill; and 0.1 g gave a 2 log viral kill.

The antimicrobial juice factors of the current invention have a number of uses. Both fruit juice and the binding agents used are considered safe for human consumption or for human skin and mucosa contact. The antimicrobials are especially useful in any treatments where bacterial growth is advantageously controlled. Such uses are in wound management where the material of the present invention can be inserted into bandages to prevent bacterial growth. It can also be directly applied to the wounds as part of a cleansing process. These novel antibacterials are also useful in treating periodontal disease where they can be used in place of antibiotics or traditional disinfectants such as peroxide. They can also be used in sanitary napkins and tampons to prevent the dangerous growth of Staphylococcus which results in Toxic Shock Syndrome.

Because the components of the instant invention are all of food grade and safe for human consumption, the insoluble juice factors are ideal as food coloring agents or as nutriceuticals. The components can be bound to a suitable binding matrix such as PVP by a batch or single step removal process. It is also possible to apply a second binding matrix to the supernatant from the first binding to effect a "secondary capture" of additional components. The components can be removed from juice or other plant homogenate and/or can be obtained from various "waste streams" which represent material normally discarded. Press cake (the material remaining after juice is pressed from fruit) can be mixed with water and/or salt solutions to release additional components that are normally discarded. The coloring components can be released (eluted) from the PVP or other binding matrix by changes in pH or ionic strength (e.g., buffers and salt solutions).

Materials produced according to the present invention should have many health benefits. They incorporate the beneficial properties of the starting materials and also have beneficial cereal and laxative properties due to the binding matrix and natural vegetable factors bound thereto. In the case of cranberry factor it is likely that ingestion will confer many of the known benefits of cranberry juice, e.g., prevention or treatment of urinary infections. The antibacterial and antiviral properties may also result in other systemic effects such as the control of undesirable intestinal bacteria. Certainly, a much greater amount of the active ingredients can be ingested as a concentrated solid than could realistically be taken in as fruit juice. In fact, the current process is able to take essentially all of the colored components from 100 pounds of cranberry fruit and concentrate it on 10 pounds of cross-linked PVP. In this process the majority of the fruit sugars and acids are discarded. This represents a ten-fold concentration. It is anticipated that further degrees of concentration can be attained.

An additional use of the material of the present invention is in food preservation. Recently there have been a number of public health scares from bacterial contamination of fruit juices and meat products such as hamburger. When used as a food color, the material of the present invention is effective in killing bacteria and preventing bacterial growth. Although coloring materials per se are generally not used in hamburger, the red coloring of the cranberry factor of the present invention is certainly compatible with hamburger. Preliminary results have indicated that mixing the cranberry factor into hamburger greatly retards spoilage of the meet. Experiments are ongoing which show that the cranberry factor can actually kill bacteria in hamburger. This is surprising and exciting because disinfection in the presence of large amounts of protein is usually very difficult or impossible.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A coloring composition produced by the steps comprising:
    a) contacting a nontoxic binding matrix selected from the group consisting of cholestyramine, starch, cross-linked starch, carboxymethyl cellulose and PVP with an aqueous juice or aqueous juice homogenate of a plant selected from the group consisting of blueberry and cranberry to obtain a mixture; and
    b) separating the remaining liquid juice from said mixture to obtain a coloring composition comprising said juice-contacted or juice homogenate-contacted binding matrix.

2. The composition of claim 1, wherein the separating step b) is carried out by decanting.

3. An antimicrobial composition produced by the steps comprising:
    a) contacting a nontoxic binding matrix selected from the group consisting of cholestyramine, starch, cross-linked starch, carboxymethyl cellulose and PVP with an aqueous juice or aqueous juice homogenate of a plant selected from the group consisting of blueberry and cranberry to obtain a mixture; and
    b) separating the remaining liquid juice from said mixture to obtain an antimicrobial composition comprising said juice-contacted or said juice homogenate-contacted binding matrix.

4. The composition of claim 3, wherein said aqueous juice is prepared by homogenizing a quantity of a presscake of said plant material in water, centrifuging the resulting mixture to produce a supernatant; and decanting said supernatant to make said aqueous juice.

5. An antimicrobial tampon produced by contacting a tampon with an antimicrobially effective amount of a composition comprising a juice-contacted binding matrix produced the steps comprising:
    a) contacting a nontoxic binding matrix selected from the group consisting of cholestyramine, starch, cross-linked starch, carboxymethyl cellulose and PVP with an aqueous juice or aqueous juice homogenate of a plant selected from the group consisting of blueberry and cranberry to obtain a mixture; and
    b) separating the remaining liquid juice from said mixture to obtain an antimicrobial composition comprising said juice-contacted or juice homogenate-contacted binding matrix.

6. The antimicrobial tampon of claim 5, wherein the matrix is PVP.

7. The antimicrobial tampon of claim 5, wherein the matrix is cholestyramine.

8. A method for producing an antimicrobial composition comprising the steps:
   a) contacting a nontoxic binding matrix selected from the group consisting of cholestyramine, starch, cross-linked starch, carboxymethyl cellulose and PVP with an aqueous juice or aqueous juice homogenate of a plant selected from the group consisting of blueberry and cranberry to obtain a mixture; and
   b) separating the remaining liquid juice from said mixture to obtain an antimicrobial composition comprising said juice-contacted or said juice homogenate-contacted binding matrix.

9. The method of claim 8, wherein the composition obtained in step b) is dried.

10. The method of claim 8, wherein the matrix is PVP.

11. The method of claim 8, wherein the matrix is cholestyramine.

12. The method of claim 8, wherein said aqueous juice is prepared by homogenizing a quantity of a presscake of said plant material in water, centrifuging the resulting mixture to produce a supernatant; and decanting said supernatant to make said aqueous juice.

* * * * *